United States Patent [19]

Sharvit et al.

[11] Patent Number: 4,801,716

[45] Date of Patent: Jan. 31, 1989

[54] PROCESS FOR PREPARING 2,3,4,5-TETRACHLORO-6-(TRI-CHLOROMETHYL) PYRIDINE

[75] Inventors: Joseph Sharvit; David Lubetzky, both of Beer Sheva, Israel

[73] Assignee: Makhteshim Chemical Works Ltd., Beer Sheva, Israel

[21] Appl. No.: 32,439

[22] Filed: Mar. 30, 1987

[51] Int. Cl.$^4$ ............................................. C07D 213/61
[52] U.S. Cl. .................................................... 546/345
[58] Field of Search .......................................... 546/345

[56] References Cited

U.S. PATENT DOCUMENTS 4,241,213 12/1980 Nishiyama et al. ................. 546/345
4,517,369 5/1985 Marinak et al. ..................... 546/345

Primary Examiner—Alan L. Rotman
Assistant Examiner—Robert C. Whittenbaugh
Attorney, Agent, or Firm—Browdy and Neimark

[57] ABSTRACT

Heptachloropicoline is prepared by continuously reacting chlorine in the gas phase at an elevated temperature with one or more lower-chlorinated 6-trichloromethyl pyridines in the presence of an effective amount of ferric chloride.

24 Claims, No Drawings

PROCESS FOR PREPARING 2,3,4,5-TETRACHLORO-6-(TRICHLOROMETHYL) PYRIDINE

BACKGROUND OF THE INVENTION

The present invention concerns the improved process for the preparation of 2,3,4,5-tetrachloro-6-(trichloromethyl)pyridine, hereinafter referred to as heptachloropicoline.

Heptachloropicoline is a known compound having been previously prepared by a number of processes. This compound has uses as a pesticide; and is also employed as a chemical intermediate in the preparation of other highly desired pesticide products. Previous methods for preparing this compound include those described in the following patents as well as the prior art noted therein. U.S. Pat. No. 3,256,167; 3,420,833; 3,732,230; 4,227,001; and 4,256,894.

Thus, U.S. Pat. No. 3,256,167 describes the continuous liquid-phase reaction of alpha-picoline hydrochloride with chlorine preferably in the presence of a Lewis catalyst or under UV radiation. However, this process requires a large excess of chlorine and a long reaction time.

U.S. Pat. No. 3,420,833 describes a process for preparing polychlorinated aromatic heterocyclic nitrogen compounds whereby alpha-picoline is reacted in the gas phase with gaseous chlorine at a temperature of from 400° C. to 700° C. A large excess of chlorine is required; but heptachloropicoline is neither mentioned nor exemplified.

U.S. Pat. No. 3,732,230 describes the reaction of liquid alpha-picoline hydrochloride with chlorine under a pressure of hydrogen chloride. However, this reaction must be run under pressure as well as requiring a reaction time of from 6 to 18 hours.

U.S. Pat. No. 4,227,001 describes the liquid phase reaction of 2,4-dichloro-6-(trichloromethyl) pyridine with chlorine at a temperature up to 220° C. in the presence of a Lewis acid catalyst and at superatmospheric pressure. Here too, reaction times of about eight hours are required.

U.S. Pat. No. 4,256,894 describes the reaction of a chloro-substituted 6-(trichloromethyl)pyridine in the liquid state with chlorine in the presence of a Lewis acid catalyst. However, here too long reaction times are required, and the heptachloropicoline is obtained in very low yield in a mixture of other chlorinated pyridines.

OBJECTIVES OF THE INVENTION

It is the objective of the present invention to provide a new and improved method for the production of heptachloropicoline. It is a further objective of the present invention to provide a method more economical than known methods for the production of this compound substantially free of pentachloropyridine in yields far in excess of those previously obtained in known methods.

SUMMARY OF THE INVENTION

It has unexpectedly been discovered that heptachloropicoline can be prepared by continuously reacting chlorine with one or more lower chlorinated picolines chosen from:

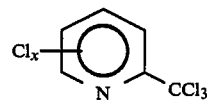

where n=1-3, comprising running the reaction at an elevated temperature in the gas phase in the presence of ferric chloride and separating the heptachloropicoline formed.

DETAILED DESCRIPTION OF THE INVENTION

The process of the present invention may be run using as a reactant one of the lower-chlorinated picolines or using a mixture containing two or more of the lower-chlorinated picolines. The lower-chlorinated picolines can be prepared by standard methods. Since the product from these standard methods is usually in the form of a mixture of lower-chlorinated picolines, it is more convenient to use such a mixture as a reactant in the process of the present invention.

In carrying out the process of the present invention, one or more of the lower-chlorinated picolines is added to an evaporator kept at a temperature of 300° C. The vapors leaving the evaporator are directed into a reactor containing chlorine, gaseous ferric chloride, and optionally a filler. A gas such as nitrogen, chlorine, or a mixture of these two and/or an inert solvent such as gaseous carbon tetrachloride may be optionally used to assist in the evaporation of the reactants in the evaporator.

The reaction of the present invention requires the use of a catalyst such as ferric chloride. However, simple coating or impregnating of the filler of the reactor is insufficient. Under the conditions of the reaction, the ferric chloride very quickly evaporates off, the result being that very little if any heptachloropicoline is formed. it is one of the surprising and novel aspects of the present invention that the chlorination of lower-chlorinated picolines affords high yields of heptachloropicoline when the ferric chloride is continuously regenerated preferably by passing gaseous ferric chloride through the reactor during the reaction. The gaseous ferric chloride can be formed by heating of the solid ferric chloride at 300° C. in the presence of a carrier gas such as nitrogen or chlorine. Alternatively, the ferric chloride may be continuously regenerated by passing chlorine gas or a mixture of chlorine and nitrogen gas over iron filings kept at a temperature of 300° C.

The gaseous ferric chloride and the gaseous lower-chlorinated picoline or mixture of these are directed into a reacctor optionally containing a filler. The reactor can be made from any material which stands up to the conditions of the present reaction. The filler serves the purpose of increasing the rate of the reaction. Thus, any inert granular or powdered material may be used, such as silica, carborundum or alumina. A preferred filler is carborundum or alumina.

While a lower limit of about 250° C. is required for the present invention, the temperature of the reaction will naturally depend upon the mole ratio of chlorine to chlorinated picolines and the residence time of the reactants. As a general rule, temperatures of from about 200° C. to about 500° C. have been found suitable for the reaction of the present invention, with a preferred temperature range of from 300° C. to 400° C., and a most preferred temperature of 350° C.

The reaction of the present invention is run in a continuous manner. The residence time will naturally depend upon the temperature, rate of adding the reactants, and type of filler used. However, residence times of from 0.1 to 5 seconds and preferably from 0.6 to 1.0 seconds are usually employed.

The reaction may be run at atmospheric pressure or at superatmospheric pressure. However, the use of superatmospheric pressure does not afford any advantage.

The process of the present invention requires the reacting of one to three moles of chlorine per mole of lower-chlorinated picolines, depending upon the type of reactant used.

For economic reasons it is preferred to use an excess of chlorine. A mole ratio of chlorine to lower-chlorinated picolines of from 2:1 to 20:1 has been found suitable; with a mole ratio of 4:1 to 15:1 most preferred.

Chlorine gas alone or in mixture with an inert gas or solvent (such as nitrogen or carbon tetrachloride) are passed simultaneously into the reactor. After passing through the reactor the product and unreacted reactants are collected by cooling and condensation in a collector kept at 0° C. The unreacted chlorine is remioved by scrubbing in caustic. Alternatively it may be optionally separated by known methods and recycled into the reactor. The resulting product is worked up and separated by standard methods to afford yields of 80–85% with conversions of 50–60%. The unreacted lower chlorined picolines may be recycled in the reaction to afford—in a very short period of time—an almostcomplete conversion of the lower-chlorinated picolines into the desired heptachloropicoline.

Thus, the present invention unexpectedly affords an inexpensive method of preparing heptachloropicoline in high yield and high conversion in a very short time, without the need for running the reaction under pressure. The process of the present invention is also advantageous in that there is a very low degradation of the product to the undesireable pentachloropyridine.

While the invention will now be described in connection with certain preferred embodiments in the following examples it will be understood that it is not intended to limit the invention to these particular embodiments. On the contrary it is intended to cover all alternatives, modifications and equivalents as may be included within the scope of the invention as defined by the appended claims.

EXAMPLES 1-4

The process of the present invention involves the use of three sections: an evaporator, a ferric chloride generator, and the main reactor as follows: (a) The lower chlorinated picolines are vaporized in an evaporator kept at 300° C. and the resulting gas swept out with carrier gases such as 30 g nitrogen per hour; 50 g chlorine per hour; or with a mixture of 17 g nitrogen and 25 g chlorine per hour. (b) The ferric chloride is formed during the reaction using a generator. This generator is conveniently made out of a glass tube having a diameter of 30 mm and a length of 150 mm filled with iron filings. While heating at 300° C., 4 g per hour of chlorine gas and 13 g per hour of nitrogen gas are passed through the tube to afford 0.03 moles of ferric chloride per hour. (c) The main reactor is conveniently a tube 67 cm in length with a diameter of 30 mm, filled with either carborundum or alumina, preferably precoated with ferric chloride.

Using the above described sections, the gaseous lower-chlorinated picolines, the simultaneously formed gaseous ferric chloride, and additional chlorine gas alone or together with nitrogen or carbon tetrachloride are passed into the main reactor kept at 350° C. using a residence time of 0.6 sec. to obtain the results summarized and shown in Table 1.

EXAMPLE 5

Following the method of Examples 1–4 a mixture of pentachloropicolines was reacted at 350° C. over carborundum coated with ferric chloride. After a few minutes practically no heptachloropicoline is formed, as the ferric chloride evaporators off the carborundum under the conditions of the reaction.

TABLE 1

| EXAMPLE | TYPE OF CHLORINATED MIXTURE[a] | MOLES/HR | CHLORINE MOLES/HR | NITROGEN MOLES/HR | CTC[b] MOLES/HR | PRODUCTS OBTAINED (MOLE PERCENT) | | | |
|---|---|---|---|---|---|---|---|---|---|
| | | | | | | Cl7 | Cl6 | Cl4 + Cl5 | Cl5Py |
| 1 | I | 0.043 | 0.4 | 0.7 | 0.7 | 63.8 | 20.3 | 12.1 | 3.8 |
| 2 | I | 0.027 | 0.4 | 1.6 | 0.5 | 68 | 17.5 | 7.7 | 6.8 |
| 3 | I | 0.03 | 0.4 | 1.0 | 0.4 | 74.2 | 14.6 | 6.3 | 4.9 |
| 4 | II | 0.15 | 0.7 | 1.6 | — | 77.2 | 6.2 | 8 | 8.6 |

[a]Key:  Mole Percent
|     | I    | II   |
|-----|------|------|
| Cl7 | 3.6  | 5.9  |
| Cl6 | 27.8 | 19.7 |
| Cl5 | 52.2 | 49.5 |
| Cl4 | 16.9 | 24.9 |

[b]CTC = Carbon tetrachloride as optional carrier gas.

[c]Key:
Cl7 = heptachloropicoline
Cl6 = hexachloropicolines
Cl4 + Cl5 = mixture of tetrachloropicolines and pentachloropicolines
Cl5Py = Pentachloropyridine

We claim:

1. A process for preparing heptachloropicoline which comprises continuously reacting chlorine with one or more lower-chlorinated picolines chosen from

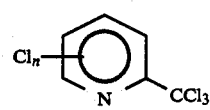

where n=1–3, wherein the reaction is conducted at an elevated temperature in the gas phase in the presence of gaseous ferric chloride, and separating the heptachloropicoline formed.

2. A process in accordance with claim 1, wherein a mixture of tetra-, penta-, and hexachloropicolines having an average of five chlorine atoms are used.

3. A process in accordance with claim 1 wherein the reaction temperature is in the range of from 250° C. to 500° C.

4. A process in accordance with claim 3 wherein the reaction temperature is in the range of from 300° C. to 400° C.

5. A process in accordance with claim 1 wherein the reaction is run over a filler.

6. A process in accordance with claim 5 wherein the filler is selected from the group consisting of silica, carborundum, and alumina.

7. A process in accordance with claim 6 wherein the filler is selected from the group consisting of carborundum and alumina.

8. A process in accordance with claim 1 wherein the ferric chloride is continuously regenerated during the reaction.

9. A process in accordance with claim 8 wherein the regeneration of ferric chloride is carried out by passing ferric chloride vapors through the reactor.

10. A process in accordance with claim 1 wherein the mole ratio of chlorine to lower-chlorinated picolines is in the ratio of from 2:1 to 20:1.

11. A process in accordance with claim 10 wherein the mole ratio of chlorine to lower-chlorinated picolines is in the ratio of from 4:1 to 15:1.

12. A process for preparing heptachloropicoline which comprises continuously reacting chlorine with one or more lower-chlorinated picolines chosen from

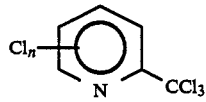

where n=1–3, wherein the reactin is conducted in the gas phase at a temperature between 300° C. and 400° C. in the presence of continuously formed gaseous ferric chloride, and separating the heptachloropicoline formed.

13. A process in accordance with claim 12 wherein a mixture of tetra-, penta-, and hexachloropicolines having an average of five chlorine atoms are used.

14. A process in accordance with claim 12 wherein the reaction is run over a filler.

15. A process in accordance with claim 14 wherein the filler is selected from the group consisting of silica, carborundum, and alumina.

16. A process in accordance with claim 15 wherein the filler is selected from the group consisting of carborundum and alumina.

17. A process in accordance with claim 12 wherein the regeneration of ferric chloride is carried out by passing ferric chloride vapors through the reactor.

18. A process in accordance with claim 12 wherein the mole ratio of chlorine to lower-chlorinated picolines is in the ratio of from 2:1 to 20:1.

19. A process in accordance with claim 18 wherein the mole ratio of chlorine to lower-chlorinated picolines is in the ratio of from 4:1 to 15:1.

20. A process for preparing heptachloropicoline which comprises continuously reacting chlorine with a mixture of tetra-, penta-, and hexachloropicolines containing an average of five chlorine atoms chosen from:

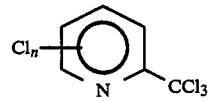

where n=1–3 wherein the reaction is conducted in the gas phase at a temperature between 300° C. and 400° C. in the presence of a filler chosen from the group consisting of carborundum and alumina, and in the presence of continuously formed gaseous ferric chloride, and separating the heptachloropicoline formed.

21. A process in accordance with claim 20 wherein the regeneration of ferric chloride is carried out by passing ferric chloride vapors through the reactor.

22. A process in accordance with claim 20 wherein the mole ratio of chlorine to lower-chlorinated picolines is in the ratio of from 2:1 to 20:1.

23. A process in accordance with claim 22 wherein the mole ratio of chlorine to lower-chlorinated picolines is in the ratio of from 4:1 to 15:1.

24. A process according to claim 1 wherein said gaseous ferric chloride is maintained continuously and a residence time of 0.1 to 5 seconds is employed.

* * * * *

UNITED STATES PATENT AND TRADEMARK OFFICE
CERTIFICATE OF CORRECTION

PATENT NO. : 4,801,716

DATED : January 31, 1989

INVENTOR(S) : SHARVIT et al.

It is certified that error appears in the above-identified patent and that said Letters Patent is hereby corrected as shown below:

| | |
|---|---|
| Column 1, line 17 | Delete "thiscompound", insert therefor -- this compound -- |
| Column 2, line 5 | In figure, Delete "$Cl_x$", insert therefor -- $Cl_n$" -- |
| Column 2, line 41 | Delete "it", insert therefor -- It -- |
| Column 3, line 25 | Delete "remi", insert therefor -- remo -- |
| Column 3, line 31 | Delete "chlorined", insert therefor -- chlorinated -- |
| Column 3, line 48 | Delete "mostcomplete", insert therefor -- most complete -- |
| Column 4, line 30 | Delete "evaporators", insert therefor -- evaporates -- |
| Column 4, line 34 | Delete "(mole percent)", insert therefor -- (mole percent)$^c$ -- |

UNITED STATES PATENT AND TRADEMARK OFFICE
CERTIFICATE OF CORRECTION

PATENT NO. : 4,801,716

DATED : January 31, 1989

INVENTOR(S) : Sharvit, et al

It is certified that error appears in the above-identified patent and that said Letters Patent is hereby corrected as shown below:

Column 5, line 36  Delete "reactin", insert therefor --reaction--

Signed and Sealed this

Thirteenth Day of August, 1991

Attest:

HARRY F. MANBECK, JR.

*Attesting Officer*  *Commissioner of Patents and Trademarks*